United States Patent
Martin et al.

(10) Patent No.: US 10,022,120 B2
(45) Date of Patent: Jul. 17, 2018

(54) SURGICAL NEEDLE WITH RECESSED FEATURES

(71) Applicant: Ethicon Endo-Surgery, LLC, Guaynabo, PR (US)

(72) Inventors: David T. Martin, Milford, OH (US); Frank R. Cichocki, Jr., Easton, PA (US); Thomas Nering, Milford, NJ (US); James M. Dick, Flowery Branch, GA (US)

(73) Assignee: ETHICON LLC, Guaynabo, PR (US)

( * ) Notice: Subject to any disclaimer, the term of this patent is extended or adjusted under 35 U.S.C. 154(b) by 292 days.

(21) Appl. No.: 14/721,244

(22) Filed: May 26, 2015

(65) Prior Publication Data

US 2016/0345958 A1 Dec. 1, 2016

(51) Int. Cl.
*A61B 17/04* (2006.01)
*A61B 17/06* (2006.01)
*A61B 17/00* (2006.01)

(52) U.S. Cl.
CPC .... *A61B 17/0469* (2013.01); *A61B 17/06066* (2013.01); *A61B 2017/00398* (2013.01); *A61B 2017/00526* (2013.01); *A61B 2017/0608* (2013.01)

(58) Field of Classification Search
CPC .... A61B 17/09099; A61B 2017/00398; A61B 2017/00526; A61B 17/0469
USPC .......................................... 606/144
See application file for complete search history.

(56) References Cited

U.S. PATENT DOCUMENTS

| | | | |
|---|---|---|---|
| 1,203,244 | A | 10/1916 | Nash |
| 1,579,379 | A | 4/1926 | Marbel |
| 1,822,330 | A | 9/1931 | Ainslie |
| 1,884,149 | A | 10/1932 | Nullmeyer |
| 2,291,181 | A | 7/1942 | Alderman |
| 3,168,097 | A | 2/1965 | Dormia |
| 3,598,281 | A | 8/1971 | Watermeier |
| 3,749,238 | A | 7/1973 | Taylor |

(Continued)

FOREIGN PATENT DOCUMENTS

| | | |
|---|---|---|
| CN | 101243985 A | 8/2008 |
| CN | 101264027 A | 9/2008 |

(Continued)

OTHER PUBLICATIONS

U.S. Appl. No. 13/792,976, filed Mar. 11, 2013 by Ethicon Endo-Surgery, Inc.

(Continued)

*Primary Examiner* — Alexander Orkin

(57) ABSTRACT

A surgical needle is adapted for use with a circular needle applier having a needle driver. The surgical needle comprises an elongate body curved along a circular arc in a plane. The elongate body has a leading end, a trailing end, a longitudinal axis between the leading and trailing ends, a cross-sectional circumference, an upper face, a lower face, a medial face, and a lateral face. A pair of recessed features on the body are adapted to be engaged by a needle driver. A pair of protuberances are adjacent each recessed feature. The protuberances are longitudinally coincident with the respective recessed feature and circumferentially offset from the respective recessed feature. The protuberances project outwardly from the body.

1 Claim, 8 Drawing Sheets

(56) References Cited

U.S. PATENT DOCUMENTS

| | | |
|---|---|---|
| 4,027,608 A | 6/1977 | Arbuckle |
| 4,123,982 A | 11/1978 | Bess, Jr. et al. |
| 4,196,836 A | 4/1980 | Becht |
| 4,203,430 A | 5/1980 | Takahashi |
| 4,235,177 A | 11/1980 | Arbuckle |
| 4,239,308 A | 12/1980 | Bradley |
| 4,406,237 A | 9/1983 | Eguchi et al. |
| 4,417,532 A | 11/1983 | Yasukata |
| 4,440,171 A | 4/1984 | Nomoto et al. |
| 4,557,265 A | 12/1985 | Andersson |
| 4,624,254 A | 11/1986 | McGarry et al. |
| 4,880,015 A | 11/1989 | Nierman |
| 4,890,614 A | 1/1990 | Kawada et al. |
| 4,899,746 A | 2/1990 | Brunk |
| 4,942,866 A | 7/1990 | Usami |
| 5,020,514 A | 6/1991 | Heckele |
| 5,133,723 A | 7/1992 | Li et al. |
| 5,209,747 A | 5/1993 | Knoepfler |
| 5,282,806 A | 2/1994 | Haber et al. |
| 5,289,963 A | 3/1994 | McGarry et al. |
| 5,306,281 A | 4/1994 | Beurrier |
| 5,308,353 A | 5/1994 | Beurrier |
| 5,312,023 A | 5/1994 | Green et al. |
| 5,318,578 A | 6/1994 | Hasson |
| 5,330,502 A | 7/1994 | Hassler et al. |
| 5,344,061 A | 9/1994 | Crainich |
| 5,383,888 A | 1/1995 | Zvenyatsky et al. |
| 5,389,103 A | 2/1995 | Melzer et al. |
| 5,403,347 A | 4/1995 | Roby et al. |
| 5,403,354 A | 4/1995 | Adams et al. |
| 5,437,681 A | 8/1995 | Meade et al. |
| 5,454,823 A | 10/1995 | Richardson et al. |
| 5,458,609 A | 10/1995 | Gordon et al. |
| 5,470,338 A | 11/1995 | Whitfield et al. |
| 5,478,344 A | 12/1995 | Stone et al. |
| 5,478,345 A | 12/1995 | Stone et al. |
| 5,480,406 A | 1/1996 | Nolan et al. |
| 5,527,321 A | 6/1996 | Hinchliffe |
| 5,540,704 A | 7/1996 | Gordon et al. |
| 5,540,705 A | 7/1996 | Meade et al. |
| 5,540,706 A | 7/1996 | Aust et al. |
| 5,549,542 A | 8/1996 | Kovalcheck |
| 5,553,477 A | 9/1996 | Eisensmith et al. |
| 5,554,170 A | 9/1996 | Roby et al. |
| 5,560,532 A | 10/1996 | DeFonzo et al. |
| 5,569,301 A | 10/1996 | Granger et al. |
| 5,571,090 A | 11/1996 | Sherts |
| 5,591,181 A | 1/1997 | Stone et al. |
| 5,593,421 A | 1/1997 | Bauer |
| 5,607,450 A | 3/1997 | Zvenyatsky et al. |
| 5,610,653 A | 3/1997 | Abecassis |
| 5,617,952 A | 4/1997 | Kranendonk |
| 5,630,825 A | 5/1997 | de la Torre et al. |
| 5,632,432 A | 5/1997 | Schulze et al. |
| 5,632,746 A | 5/1997 | Middleman et al. |
| 5,643,295 A | 7/1997 | Yoon |
| 5,645,552 A | 7/1997 | Sherts |
| 5,649,961 A | 7/1997 | McGregor et al. |
| 5,665,096 A | 9/1997 | Yoon |
| 5,665,109 A | 9/1997 | Yoon |
| 5,669,490 A | 9/1997 | Colligan et al. |
| 5,674,229 A | 10/1997 | Tovey et al. |
| 5,674,230 A | 10/1997 | Tovey et al. |
| 5,693,071 A | 12/1997 | Gorecki et al. |
| 5,702,408 A | 12/1997 | Wales et al. |
| 5,707,379 A | 1/1998 | Fleenor et al. |
| 5,709,693 A | 1/1998 | Taylor |
| 5,713,910 A | 2/1998 | Gordon et al. |
| 5,728,107 A | 3/1998 | Zlock et al. |
| 5,728,108 A | 3/1998 | Griffiths et al. |
| 5,728,109 A | 3/1998 | Schulze et al. |
| 5,733,293 A | 3/1998 | Scirica et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,766,196 A | 6/1998 | Griffiths |
| 5,776,186 A | 7/1998 | Uflacker |
| 5,792,135 A | 8/1998 | Madhani et al. |
| 5,792,151 A | 8/1998 | Heck et al. |
| 5,797,927 A | 8/1998 | Yoon |
| 5,814,054 A | 9/1998 | Kortenbach et al. |
| 5,814,069 A | 9/1998 | Schulze et al. |
| 5,817,084 A | 10/1998 | Jensen |
| 5,846,254 A | 12/1998 | Schulze et al. |
| 5,860,992 A | 1/1999 | Daniel et al. |
| 5,865,836 A | 2/1999 | Miller |
| 5,871,488 A | 2/1999 | Tovey et al. |
| 5,878,193 A | 3/1999 | Wang et al. |
| 5,888,192 A | 3/1999 | Heimberger |
| 5,897,563 A | 4/1999 | Yoon et al. |
| 5,904,667 A | 5/1999 | Falwell |
| 5,908,428 A | 6/1999 | Scirica et al. |
| 5,911,727 A | 6/1999 | Taylor |
| 5,921,956 A | 7/1999 | Grinberg et al. |
| 5,938,668 A | 8/1999 | Scirica et al. |
| 5,941,430 A | 8/1999 | Kuwabara |
| 5,944,724 A | 8/1999 | Lizardi |
| 5,947,982 A | 9/1999 | Duran |
| 5,954,731 A | 9/1999 | Yoon |
| 5,954,733 A | 9/1999 | Yoon |
| 5,976,074 A | 11/1999 | Moriyama |
| 5,993,381 A | 11/1999 | Ito |
| 5,993,466 A | 11/1999 | Yoon |
| 6,016,905 A | 1/2000 | Gemma et al. |
| 6,053,908 A | 4/2000 | Crainich et al. |
| 6,056,771 A | 5/2000 | Proto |
| 6,071,289 A | 6/2000 | Stefanchik et al. |
| 6,086,601 A | 7/2000 | Yoon |
| 6,096,051 A | 8/2000 | Kortenbach et al. |
| 6,126,666 A | 10/2000 | Trapp et al. |
| 6,129,741 A | 10/2000 | Wurster et al. |
| 6,135,385 A | 10/2000 | Martinez de Lahidalga |
| 6,136,010 A | 10/2000 | Modesitt et al. |
| 6,138,440 A | 10/2000 | Gemma |
| 6,152,934 A | 11/2000 | Harper et al. |
| 6,162,208 A | 12/2000 | Hipps |
| 6,214,030 B1 | 4/2001 | Matsutani et al. |
| 6,231,565 B1 | 5/2001 | Tovey et al. |
| 6,332,888 B1 | 12/2001 | Levy et al. |
| 6,332,889 B1 | 12/2001 | Sancoff et al. |
| 6,364,888 B1 | 4/2002 | Niemeyer et al. |
| 6,443,962 B1 | 9/2002 | Gaber |
| 6,454,778 B2 | 9/2002 | Kortenbach |
| 6,481,568 B1 | 11/2002 | Cerwin et al. |
| 6,533,112 B2 | 3/2003 | Warnecke |
| 6,719,763 B2 | 4/2004 | Chung et al. |
| 6,719,764 B1 | 4/2004 | Gellman et al. |
| 6,743,239 B1 | 6/2004 | Kuehn et al. |
| 6,755,843 B2 | 6/2004 | Chung et al. |
| 6,783,524 B2 | 8/2004 | Anderson et al. |
| 6,783,537 B1 | 8/2004 | Kuhr et al. |
| D496,997 S | 10/2004 | Dycus et al. |
| 6,923,819 B2 | 8/2005 | Meade et al. |
| 6,936,054 B2 | 8/2005 | Chu |
| 6,939,358 B2 | 9/2005 | Palacios et al. |
| 6,955,643 B2 | 10/2005 | Gellman et al. |
| 7,004,951 B2 | 2/2006 | Gibbens, III |
| 7,022,085 B2 | 4/2006 | Cooke et al. |
| 7,041,111 B2 | 5/2006 | Chu |
| 7,131,979 B2 | 11/2006 | DiCarlo et al. |
| 7,144,401 B2 | 12/2006 | Yamamoto et al. |
| 7,232,447 B2 | 6/2007 | Gellman et al. |
| 7,235,087 B2 | 6/2007 | Modesitt et al. |
| 7,278,563 B1 | 10/2007 | Green |
| 7,338,504 B2 | 3/2008 | Gibbens, III et al. |
| 7,442,198 B2 | 10/2008 | Gellman et al. |
| 7,491,166 B2 | 2/2009 | Ueno et al. |
| 7,520,382 B2 | 4/2009 | Kennedy et al. |
| 7,524,320 B2 | 4/2009 | Tierney et al. |
| D594,983 S | 6/2009 | Price et al. |
| 7,582,096 B2 | 9/2009 | Gellman et al. |
| 7,588,583 B2 | 9/2009 | Hamilton et al. |
| 7,604,611 B2 | 10/2009 | Falwell et al. |

(56) References Cited

U.S. PATENT DOCUMENTS

| | | |
|---|---|---|
| 7,615,060 B2 | 11/2009 | Stokes et al. |
| 7,628,796 B2 | 12/2009 | Shelton, IV et al. |
| 7,637,369 B2 | 12/2009 | Kennedy et al. |
| 7,666,194 B2 | 2/2010 | Field et al. |
| 7,686,831 B2 | 3/2010 | Stokes et al. |
| 7,691,095 B2 | 4/2010 | Bednarek et al. |
| 7,691,098 B2 | 4/2010 | Wallace et al. |
| 7,699,860 B2 | 4/2010 | Huitema et al. |
| 7,703,653 B2 | 4/2010 | Shah et al. |
| 7,763,036 B2 | 7/2010 | Stokes et al. |
| 7,766,925 B2 | 8/2010 | Stokes et al. |
| 7,770,365 B2 | 8/2010 | Enriquez, III et al. |
| 7,806,891 B2 | 10/2010 | Nowlin et al. |
| 7,815,654 B2 | 10/2010 | Chu |
| 7,824,401 B2 | 11/2010 | Manzo et al. |
| 7,828,812 B2 | 11/2010 | Stokes et al. |
| 7,833,235 B2 | 11/2010 | Chu |
| 7,833,236 B2 | 11/2010 | Stokes et al. |
| 7,842,048 B2 | 11/2010 | Ma |
| 7,846,169 B2 | 12/2010 | Shelton, IV et al. |
| 7,857,812 B2 | 12/2010 | Dycus et al. |
| 7,862,572 B2 | 1/2011 | Meade et al. |
| 7,862,575 B2 | 1/2011 | Tal |
| 7,862,582 B2 | 1/2011 | Ortiz et al. |
| D631,965 S | 2/2011 | Price et al. |
| 7,887,554 B2 | 2/2011 | Stokes et al. |
| 7,891,485 B2 | 2/2011 | Prescott |
| 7,896,890 B2 | 3/2011 | Ortiz et al. |
| 7,909,220 B2 | 3/2011 | Viola |
| 7,922,063 B2 | 4/2011 | Zemlok et al. |
| 7,935,128 B2 | 5/2011 | Rioux et al. |
| 7,942,886 B2 | 5/2011 | Alvarado |
| 7,947,052 B2 | 5/2011 | Baxter, III et al. |
| 7,976,553 B2 | 7/2011 | Shelton, IV et al. |
| 7,976,555 B2 | 7/2011 | Meade et al. |
| 7,993,354 B1 | 8/2011 | Brecher et al. |
| 8,012,161 B2 | 9/2011 | Primavera et al. |
| 8,016,840 B2 | 9/2011 | Takemoto et al. |
| 8,021,375 B2 | 9/2011 | Aldrich et al. |
| 8,048,092 B2 | 11/2011 | Modesitt et al. |
| 8,057,386 B2 | 11/2011 | Aznoian et al. |
| 8,066,737 B2 | 11/2011 | Meade et al. |
| 8,100,922 B2 | 1/2012 | Griffith |
| 8,118,820 B2 | 2/2012 | Stokes et al. |
| 8,123,762 B2 | 2/2012 | Chu et al. |
| 8,123,764 B2 | 2/2012 | Meade et al. |
| 8,136,656 B2 | 3/2012 | Kennedy et al. |
| 8,187,288 B2 | 5/2012 | Chu et al. |
| 8,196,739 B2 | 6/2012 | Kirsch |
| 8,201,721 B2 | 6/2012 | Zemlok et al. |
| 8,206,284 B2 | 6/2012 | Aznoian et al. |
| 8,211,143 B2 | 7/2012 | Stefanchik et al. |
| 8,236,010 B2 | 8/2012 | Ortiz et al. |
| 8,236,013 B2 | 8/2012 | Chu |
| 8,241,320 B2 | 8/2012 | Lyons et al. |
| 8,246,637 B2 | 8/2012 | Viola et al. |
| 8,252,008 B2 | 8/2012 | Ma |
| 8,256,613 B2 | 9/2012 | Kirsch et al. |
| 8,257,369 B2 | 9/2012 | Gellman et al. |
| 8,257,371 B2 | 9/2012 | Hamilton et al. |
| 8,292,067 B2 | 10/2012 | Chowaniec et al. |
| 8,292,906 B2 | 10/2012 | Taylor et al. |
| 8,307,978 B2 | 11/2012 | Kirsch et al. |
| 8,333,776 B2 | 12/2012 | Cheng et al. |
| 8,361,089 B2 | 1/2013 | Chu |
| 8,366,725 B2 | 2/2013 | Chu |
| 8,372,090 B2 | 2/2013 | Wingardner et al. |
| 8,398,660 B2 | 3/2013 | Chu et al. |
| 8,460,320 B2 | 6/2013 | Hirzel |
| 8,469,973 B2 | 6/2013 | Meade et al. |
| 8,474,522 B2 | 7/2013 | Lynde et al. |
| 8,490,713 B2 | 7/2013 | Furnish et al. |
| 8,500,756 B2 | 8/2013 | Papa et al. |
| 8,512,243 B2 | 8/2013 | Stafford |
| 8,518,058 B2 | 8/2013 | Gellman et al. |
| 8,551,122 B2 | 10/2013 | Lau |
| 8,556,069 B2 | 10/2013 | Kirsch |
| 8,562,630 B2 | 10/2013 | Campbell |
| 8,568,428 B2 | 10/2013 | McClurg et al. |
| 8,579,918 B2 | 11/2013 | Whitfield et al. |
| 8,603,089 B2 | 12/2013 | Viola |
| 8,623,027 B2 | 1/2014 | Price et al. |
| 8,623,048 B2 | 1/2014 | Brecher et al. |
| 8,641,728 B2 | 2/2014 | Stokes et al. |
| 8,663,253 B2 | 3/2014 | Saliman |
| 8,696,687 B2 | 4/2014 | Gellman et al. |
| 8,702,729 B2 | 4/2014 | Chu |
| 8,702,732 B2 | 4/2014 | Woodard, Jr. et al. |
| 8,709,021 B2 | 4/2014 | Chu et al. |
| 8,746,445 B2 | 6/2014 | Kennedy et al. |
| 8,747,304 B2 | 6/2014 | Zeiner et al. |
| D709,194 S | 7/2014 | Millet et al. |
| 8,771,295 B2 | 7/2014 | Chu |
| 8,821,518 B2 | 9/2014 | Saliman et al. |
| 8,821,519 B2 | 9/2014 | Meade et al. |
| 8,833,549 B2 | 9/2014 | Kirsch |
| 8,858,572 B2 | 10/2014 | Klundt et al. |
| D716,945 S | 11/2014 | Miller et al. |
| 8,906,043 B2 | 12/2014 | Woodard, Jr. et al. |
| 8,920,440 B2 | 12/2014 | McClurg et al. |
| 8,920,441 B2 | 12/2014 | Saliman |
| 8,925,783 B2 | 1/2015 | Zemlok et al. |
| 8,968,337 B2 | 3/2015 | Whitfield et al. |
| 9,060,769 B2 | 6/2015 | Coleman et al. |
| 9,113,861 B2 | 8/2015 | Martin et al. |
| 9,113,876 B2 | 8/2015 | Zemlok et al. |
| 9,125,645 B1 | 9/2015 | Martin et al. |
| 9,168,037 B2 | 10/2015 | Woodard, Jr. et al. |
| 9,173,655 B2 | 11/2015 | Martin |
| 9,220,496 B2 | 12/2015 | Martin et al. |
| 9,241,712 B2 | 1/2016 | Zemlok et al. |
| 9,247,938 B2 | 2/2016 | Martin et al. |
| 9,277,916 B2 | 3/2016 | Martin et al. |
| 9,289,206 B2 | 3/2016 | Hess et al. |
| D754,856 S | 4/2016 | Martin et al. |
| 9,314,292 B2 | 4/2016 | Trees et al. |
| 9,351,754 B2 | 5/2016 | Vakharia et al. |
| 9,427,226 B2 | 8/2016 | Martin et al. |
| 9,427,228 B2 | 8/2016 | Hart |
| 9,554,793 B2 | 1/2017 | Lane et al. |
| 2001/0025134 A1 | 9/2001 | Bon et al. |
| 2001/0027312 A1 | 10/2001 | Bacher et al. |
| 2002/0138084 A1 | 9/2002 | Weber |
| 2002/0193809 A1 | 12/2002 | Meade et al. |
| 2003/0083674 A1 | 5/2003 | Gibbens, III |
| 2003/0208100 A1 | 11/2003 | Levy |
| 2003/0233104 A1 | 12/2003 | Gellman et al. |
| 2004/0050721 A1 | 3/2004 | Roby et al. |
| 2004/0172047 A1 | 9/2004 | Gellman et al. |
| 2004/0260314 A1 | 12/2004 | Lizardi et al. |
| 2005/0015101 A1 | 1/2005 | Gibbens, III et al. |
| 2005/0216038 A1 | 9/2005 | Meade et al. |
| 2006/0036232 A1 | 2/2006 | Primavera et al. |
| 2006/0047309 A1 | 3/2006 | Cichocki, Jr. |
| 2006/0069396 A1* | 3/2006 | Meade ............... A61B 17/0482 606/144 |
| 2006/0111732 A1 | 5/2006 | Gibbens et al. |
| 2006/0173491 A1 | 8/2006 | Meade et al. |
| 2006/0259073 A1 | 11/2006 | Miyamoto et al. |
| 2006/0281970 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton, IV et al. |
| 2006/0282099 A1 | 12/2006 | Stokes et al. |
| 2007/0088372 A1 | 4/2007 | Gellman et al. |
| 2007/0162052 A1 | 7/2007 | Hashimoto et al. |
| 2007/0173864 A1 | 7/2007 | Chu |
| 2007/0256945 A1 | 11/2007 | Kennedy et al. |
| 2008/0091220 A1 | 4/2008 | Chu |
| 2008/0103357 A1 | 5/2008 | Zeiner et al. |
| 2008/0109015 A1 | 5/2008 | Chu et al. |
| 2008/0132919 A1 | 6/2008 | Chui et al. |
| 2008/0177134 A1 | 7/2008 | Miyamoto et al. |
| 2008/0228204 A1 | 9/2008 | Hamilton et al. |

(56) References Cited

U.S. PATENT DOCUMENTS

| | | |
|---|---|---|
| 2008/0243146 A1 | 10/2008 | Sloan et al. |
| 2008/0255590 A1 | 10/2008 | Meade et al. |
| 2009/0024145 A1 | 1/2009 | Meade et al. |
| 2009/0084826 A1 | 4/2009 | Shah et al. |
| 2009/0088792 A1 | 4/2009 | Hoell, Jr. et al. |
| 2009/0205987 A1 | 8/2009 | Kennedy et al. |
| 2009/0209980 A1 | 8/2009 | Harris |
| 2009/0248041 A1 | 10/2009 | Williams et al. |
| 2009/0259092 A1 | 10/2009 | Ogdahl et al. |
| 2009/0287226 A1 | 11/2009 | Gellman et al. |
| 2009/0312772 A1 | 12/2009 | Chu |
| 2010/0010512 A1 | 1/2010 | Taylor et al. |
| 2010/0016866 A1 | 1/2010 | Meade et al. |
| 2010/0023024 A1 | 1/2010 | Zeiner et al. |
| 2010/0036415 A1 | 2/2010 | Cabezas |
| 2010/0042116 A1 | 2/2010 | Chui et al. |
| 2010/0063519 A1 | 3/2010 | Park et al. |
| 2010/0078336 A1 | 4/2010 | Reyhan et al. |
| 2010/0100125 A1 | 4/2010 | Mahadevan |
| 2010/0152751 A1 | 6/2010 | Meade et al. |
| 2010/0274265 A1 | 10/2010 | Wingardner et al. |
| 2011/0028999 A1 | 2/2011 | Chu |
| 2011/0040308 A1 | 2/2011 | Cabrera et al. |
| 2011/0042245 A1 | 2/2011 | McClurg et al. |
| 2011/0046642 A1 | 2/2011 | McClurg et al. |
| 2011/0046667 A1 | 2/2011 | Culligan et al. |
| 2011/0060352 A1 | 3/2011 | Chu |
| 2011/0082476 A1 | 4/2011 | Furnish et al. |
| 2011/0288582 A1 | 11/2011 | Meade et al. |
| 2011/0295278 A1 | 12/2011 | Meade et al. |
| 2011/0313433 A1 | 12/2011 | Woodard, Jr. et al. |
| 2012/0004672 A1 | 1/2012 | Giap et al. |
| 2012/0035626 A1 | 2/2012 | Chu |
| 2012/0041456 A1 | 2/2012 | Gellman et al. |
| 2012/0055828 A1 | 3/2012 | Kennedy et al. |
| 2012/0059396 A1 | 3/2012 | Harris et al. |
| 2012/0078243 A1 | 3/2012 | Worrell et al. |
| 2012/0109163 A1 | 5/2012 | Chu et al. |
| 2012/0123471 A1 | 5/2012 | Woodard, Jr. et al. |
| 2012/0130404 A1 | 5/2012 | Meade et al. |
| 2012/0143248 A1 | 6/2012 | Brecher et al. |
| 2012/0150199 A1 | 6/2012 | Woodard, Jr. et al. |
| 2012/0165837 A1 | 6/2012 | Belman et al. |
| 2012/0165838 A1 | 6/2012 | Kobylewski et al. |
| 2012/0215234 A1 | 8/2012 | Chowaniec et al. |
| 2012/0220832 A1 | 8/2012 | Nakade et al. |
| 2012/0226292 A1 | 9/2012 | Hirzel |
| 2012/0228163 A1 | 9/2012 | Kirsch |
| 2012/0232567 A1 | 9/2012 | Fairneny |
| 2012/0283748 A1 | 11/2012 | Ortiz et al. |
| 2012/0283750 A1 | 11/2012 | Saliman et al. |
| 2012/0283755 A1 | 11/2012 | Gellman et al. |
| 2013/0041388 A1 | 2/2013 | Lane et al. |
| 2013/0158593 A1 | 6/2013 | Kiapour et al. |
| 2013/0282027 A1 | 10/2013 | Woodard, Jr. et al. |
| 2013/0282031 A1 | 10/2013 | Woodard, Jr. et al. |
| 2013/0296889 A1 | 11/2013 | Tong et al. |
| 2013/0331866 A1 | 12/2013 | Gellman et al. |
| 2014/0005681 A1 | 1/2014 | Gee et al. |
| 2014/0088621 A1 | 3/2014 | Krieger et al. |
| 2014/0166514 A1 | 6/2014 | Martin et al. |
| 2014/0171970 A1 | 6/2014 | Martin et al. |
| 2014/0171971 A1 | 6/2014 | Martin et al. |
| 2014/0171972 A1 | 6/2014 | Martin |
| 2014/0171975 A1* | 6/2014 | Martin ............... A61B 17/0483 606/145 |
| 2014/0171976 A1 | 6/2014 | Martin et al. |
| 2014/0171977 A1 | 6/2014 | Martin et al. |
| 2014/0171978 A1 | 6/2014 | Martin |
| 2014/0171979 A1 | 6/2014 | Martin et al. |
| 2014/0172015 A1 | 6/2014 | Martin et al. |
| 2014/0228865 A1* | 8/2014 | Weisel ............... A61B 17/0483 606/144 |
| 2014/0305988 A1 | 10/2014 | Boudreaux et al. |
| 2015/0127024 A1 | 5/2015 | Berry |
| 2015/0133967 A1 | 5/2015 | Martin |
| 2015/0142020 A1 | 5/2015 | Woodard, Jr. et al. |
| 2015/0351744 A1 | 12/2015 | Deck et al. |
| 2015/0351745 A1 | 12/2015 | Mumaw et al. |
| 2015/0351746 A1 | 12/2015 | Martin et al. |
| 2015/0351747 A1 | 12/2015 | Martin et al. |
| 2015/0351748 A1 | 12/2015 | White et al. |
| 2015/0351749 A1 | 12/2015 | Martin et al. |
| 2015/0351756 A1 | 12/2015 | Martin et al. |
| 2016/0120740 A1 | 5/2016 | Rawls-Meehan |
| 2016/0345958 A1 | 12/2016 | Martin et al. |
| 2016/0346827 A1 | 12/2016 | Martin et al. |
| 2016/0367238 A1 | 12/2016 | Deck et al. |
| 2016/0367243 A1 | 12/2016 | Martin et al. |

FOREIGN PATENT DOCUMENTS

| | | |
|---|---|---|
| CN | 201899530 U | 7/2011 |
| CN | 102551825 A | 7/2012 |
| CN | 202426582 U | 9/2012 |
| DE | 4310315 A1 | 10/1993 |
| DE | 4300307 A1 | 7/1994 |
| EP | 0674875 A1 | 10/1995 |
| EP | 0739184 B1 | 9/1998 |
| EP | 1791476 A2 | 6/2007 |
| EP | 2055243 A2 | 5/2009 |
| EP | 2292157 A2 | 3/2011 |
| EP | 2308391 A1 | 4/2011 |
| EP | 2792308 A2 | 10/2014 |
| FR | 2540377 A1 | 8/1984 |
| GB | 18602 A | 9/1909 |
| GB | 2389313 A | 12/2003 |
| JP | 55-151956 A | 11/1980 |
| JP | 2013-146613 A | 8/2013 |
| WO | WO 95/19149 A1 | 7/1995 |
| WO | WO 97/29694 A1 | 8/1997 |
| WO | WO 99/12482 A1 | 3/1999 |
| WO | WO 99/40850 A1 | 8/1999 |
| WO | WO 99/47050 A2 | 9/1999 |
| WO | WO 01/12084 A1 | 2/2001 |
| WO | WO 02/102226 A2 | 12/2002 |
| WO | WO 03/028541 A2 | 4/2003 |
| WO | WO 03/063712 A1 | 8/2003 |
| WO | WO 2004/012606 A1 | 2/2004 |
| WO | WO 2004/021894 A1 | 3/2004 |
| WO | WO 2004/086986 A1 | 10/2004 |
| WO | WO 2006/034209 A2 | 3/2006 |
| WO | WO 2007/089603 A2 | 8/2007 |
| WO | WO 2008/045333 A2 | 4/2008 |
| WO | WO 2008/045376 A2 | 4/2008 |
| WO | WO 2008/081474 A1 | 7/2008 |
| WO | WO 2008/147555 A2 | 12/2008 |
| WO | WO 2008/150773 A1 | 12/2008 |
| WO | WO 2010/031064 A1 | 3/2010 |
| WO | WO 2010/062380 A1 | 6/2010 |
| WO | WO 2010/127274 A1 | 11/2010 |
| WO | WO 2011/156733 A2 | 12/2011 |
| WO | WO 2012/029689 A1 | 3/2012 |
| WO | WO 2012/044998 A2 | 4/2012 |
| WO | WO 2012/068002 A1 | 5/2012 |
| WO | WO 2012/088232 A3 | 6/2012 |
| WO | WO 2013/142487 A1 | 9/2013 |
| WO | WO 2013/158622 A1 | 10/2013 |
| WO | WO 2014/147619 A1 | 9/2014 |
| WO | WO 2014/162434 A1 | 10/2014 |

OTHER PUBLICATIONS

U.S. Appl. No. 13/793,048, filed Mar. 11, 2013 by Ethicon Endo-Surgery, Inc.
U.S. Appl. No. 29/493,229, filed Jun. 6, 2014 by Ethicon Endo-Surgery, Inc.
U.S. Appl. No. 29/493,231, filed Jun. 6, 2014 by Ethicon Endo-Surgery, Inc.
U.S. Appl. No. 14/600,486, filed Jan. 20, 2015 by Ethicon Endo-Surgery, Inc.
U.S. Appl. No. 29/493,233, filed Jun. 6, 2014 by Ethicon Endo-Surgery, Inc.

(56) References Cited

OTHER PUBLICATIONS

U.S. Appl. No. 14/688,497, filed Apr. 16, 2015 by Ethicon Endo-Surgery, Inc.
U.S. Appl. No. 14/721,251, filed May 26, 2015 by Ethicon Endo-Surgery, Inc.
U.S. Appl. No. 14/741,849, filed Jun. 17, 2015 by Ethicon Endo-Surgery, Inc.
U.S. Appl. No. 29/530,605, filed Jun. 18, 2015 by Ethicon Endo-Surgery, Inc.
International Preliminary Report dated Jun. 16, 2015, International Application No. PCT/US2013/074866.
International Search Report dated May 6, 2014, International Application No. PCT/US2013/074866.
International Search Report dated Sep. 15, 2015, International Application No. PCT/US2015/031883.
International Search Report dated Sep. 28, 2015, International Application No. PCT/US2015/031911.
European Search Report dated Dec. 7, 2015; Application No. 15176796.9.
European Search Report dated Dec. 4, 2015; Application No. 15176924.7.
European Search Report dated Nov. 30, 2015; Application No. 15176774.6.
Endo 360 "Laparoscopic & Minimally Invasive Suturing Devices" Catalog—2 Pages—EndoEvolution, LLC—2011.
Covidien Endo Stitch (Features and Benefits) "Suturing Made Easy" Brochure—4 Pages—2008.
Pages from www.endoevolution.com. Printed on Jun. 3, 2014, but publication date unknown. Please treat as prior art until applicant establishes otherwise.
U.S. Appl. No. 14/298,083, filed Jun. 6, 2014 by Ethicon Endo-Surgery, Inc.
International Preliminary Report dated Dec. 6, 2016, International Application No. PCT/US2015/031883.
International Preliminary Report dated Dec. 6, 2016, International Application No. PCT/US2015/031911.
International Search Report dated Aug. 8, 2016, International Application No. PCT/US2016/033782.
International Search Report dated Jul. 29, 2016, International Application No. PCT/US2016/035390.
International Search Report dated Nov. 14, 2016, International Application No. PCT/US2016/037348.
International Search Report dated Nov. 14, 2016, International Application No. PCT/US2016/037350.
International Search Report dated Oct. 24, 2016, International Application No. PCT/US2016/037557.
European Search Report dated Feb. 3, 2016; Application No. 15176794.4.

* cited by examiner

SURGICAL NEEDLE WITH RECESSED FEATURES

BACKGROUND

The present invention relates in general to surgical devices and procedures, and more particularly to surgical suturing.

Sutures are often used in a wide variety of surgical procedures. Manual suturing is typically accomplished by the surgeon using a fine pair of graspers to grab and hold a suture needle, pierce the tissue with the needle, let go of the needle, and regrasp the needle to pull the needle and accompanying suture thread through the tissues to be sutured. Such needles are typically curved with the suture attached to the trailing end of the needle. A variety of automated suturing devices have been attempted to speed the process of suturing and to facilitate fine suturing or suturing during endoscopic, laparoscopic, or arthroscopic surgeries.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

SUMMARY

Figure 1:
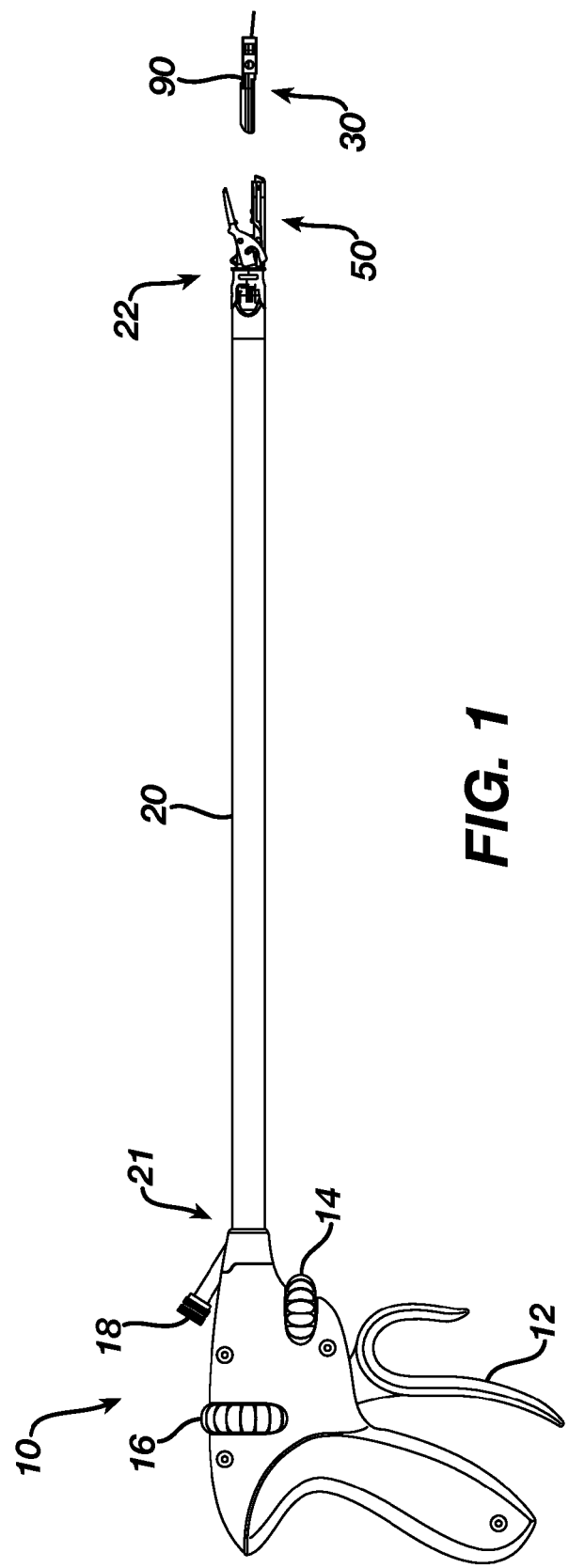
FIG. 1 depicts a side view of a surgical suturing device.

In one embodiment, a surgical needle is adapted for use with a circular needle applier having a needle driver. The surgical needle comprises an elongate body curved along a circular arc in a plane. The elongate body has a leading end, a trailing end, a longitudinal axis between the leading and trailing ends, a cross-sectional circumference, an upper face, a lower face, a medial face, and a lateral face. A pair of recessed features on the body are adapted to be engaged by a needle driver. A pair of protuberances are adjacent each recessed feature. The protuberances are longitudinally coincident with the respective recessed feature and circumferentially offset from the respective recessed feature. The protuberances project outwardly from the body.

Each recessed feature may comprise a step portion on the leading side that descends into a valley portion and a tiered surface rising from the trailing side of the valley portion. The tiered surface may comprise a flat portion and a pair of oblique portions, the flat portion being generally parallel with the longitudinal axis and intermediate the oblique portions. The apex of the protuberances may longitudinally coincide with the valley portion of the respective recessed feature.

The recessed features are on the medial face and the protuberances may be on the upper and lower faces. The pair of recessed features may be positioned at antipodal points on the circular arc. The surgical needle may further comprise a longitudinal flat on the body. The longitudinal flat may be intermediate the recessed features. The longitudinal flat and recessed features may be all circumferentially aligned. The protuberances may project about 3-10% the diameter of the body. The protuberances project about 6-8% the diameter of the body. The recessed features may be formed by a pressing operation. The recessed features may be formed without removing material from the body.

The surgical needle may further comprise a length of suture connected to the trailing end. A cartridge may comprise the surgical needle and a needle driver. The cartridge may further comprise a rotary input and a link connecting the needle driver to the rotary input.

In another embodiment, a surgical needle is adapted for use with a circular needle applier having a needle driver. The surgical needle comprises an elongate body curved along a circular arc in a plane. The elongate body has a leading end, a trailing end, a longitudinal axis between the leading and trailing ends, a cross-sectional circumference, an upper face, a lower face, a medial face, and a lateral face. A first recessed feature is on the medial face of the body adapted to be engaged by a needle driver. A first pair of protuberances project outwardly from the upper and lower faces of the body, the first pair of protuberances being longitudinally coincident with the first recessed feature. A second recessed feature is on the medial face of the body adapted to be engaged by a needle driver, the second recessed feature being located at the antipodal point of the circular arc relative the first recessed feature. A second pair of protuberances project outwardly from the upper and lower faces of the body, the second pair of protuberances being longitudinally coincident with the second recessed feature.

In yet another embodiment, a method is used for fabricating a surgical needle for use in with a circular needle applier having a needle driver. The method comprises the steps:

a) straightening and cutting a wire body to an initial length, the wire body having a first end and a second end;

b) grinding a point on the first end of the wire body;

c) plastically deforming the wire body to form two recessed features adapted to be engaged by a needle driver;

d) cutting the wire body to a final length with a trailing end;

e) drilling a hole in the trailing end to create a barrel;

f) bending the wire body along a circular arc while keeping straight a trailing portion with the barrel;

g) attaching a length of suture in the barrel; and h) bending the trailing portion along the circular arc.

The steps may be performed sequentially as listed. The method may further comprise before step (c) the step of pressing one or more longitudinal flats on the wire body. The method may further comprise between steps (f) and (g) the step of cleaning the wire body. The method may further comprise between steps (f) and (g) the step of heat treating the wire body. The method may further comprise between steps (f) and (g) the step of electro-polishing the wire body. The method may further comprise between steps (f) and (g) the step of coating the wire body with silicone. During step (f), the recessed features may be oriented medially from the wire body. The method may further comprise prior to step (d) the step of bending a tail in the second end of the wire body.

DETAILED DESCRIPTION

FIG. 1 illustrates an embodiment of a surgical suturing device. An elongate shaft (20) has a proximal end (21), a distal end (22), and a longitudinal axis extending therebetween. An actuator (10) is connected to the proximal end (21) of the shaft (20). In this embodiment the actuator (10) is a manual pistol grip handle; however, a variety of other manual actuators could also be used, including a scissor grip handle, a syringe grip handle, endoscopic rotary knobs, and the like. The actuator (10) could also take the form of a robotic interface, such as a DAVINCI puck, or a housing comprising gears or pulleys, servomechanisms, and the like.

A circular needle applier (30) is connected to the distal end (22) of the shaft (20). The circular needle applier (30) rotates an arced needle in a circular path enabling a surgeon to selectively apply sutures. The circular needle applier (30) may be integral with the shaft (20) and actuator (10) as a unitary disposable instrument intended for a single surgical procedure. The circular needle applier (30) may also be integral with the shaft (20) and actuator (10) as a reusable instrument. Optionally, as illustrated here, the circular needle applier (30) may be embodied in a disposable cartridge (90) and the shaft (20) may include a receiver (50) to hold the cartridge (90). In such an embodiment, the shaft (20) and actuator (10) may also be disposable or reusable. Embodiments with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also used with low temperature sterilization techniques known in the art.

A first input (12), shown here as a trigger that pivots between opened and closed positions, may be used to selectively actuate the circular needle applier (30). The trigger may be spring biased to return the trigger to its open position. A second input (14), shown here as a rotary knob, may be used to selectively articulate the shaft (20). A third input (16), shown here as a rotary knob, may be used to selectively rotate the circular needle applier (30) about the shaft (20). Naturally, the number, type, configuration, and operation of the inputs (12, 14, and 16) may vary.

Figure 2:
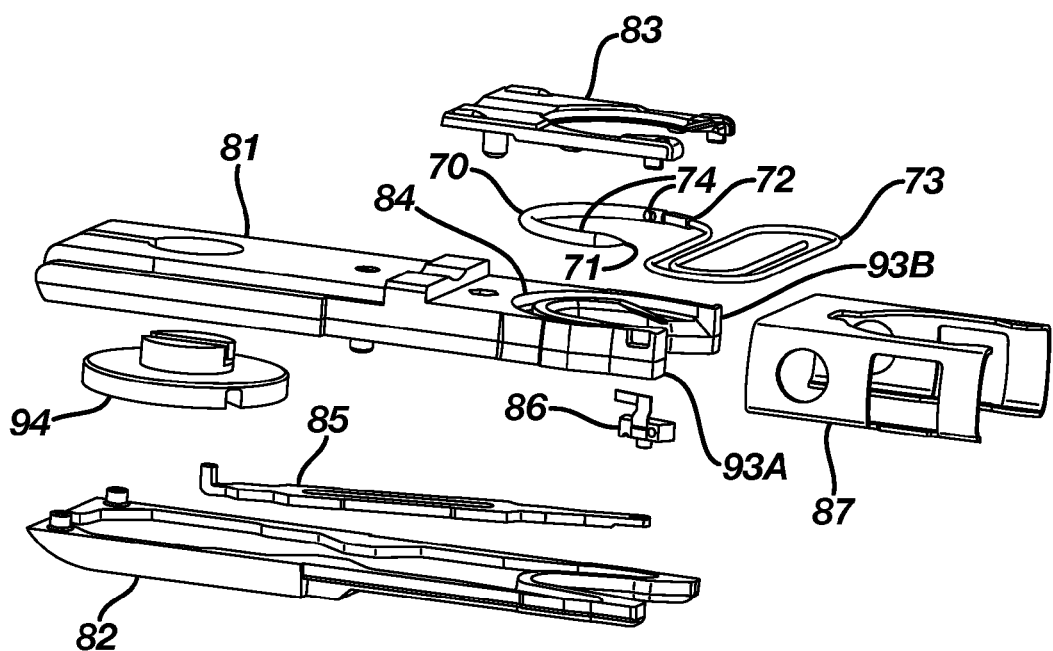
FIG. 2 depicts an exploded view of a cartridge.

FIG. 2 illustrates an example of a cartridge (90) comprising a lower body (81), an upper body (82), and a needle cover (83). The needle driver (86), rotary input (94), and link (85) are captured between the lower body (81) and an upper body (82). The lower and upper bodies (81, 82) are attached to one another using a variety of known techniques, including welds, pins, adhesives, and the like to form the cartridge body. The needle (70) has a leading end (71) and a length of suture (73) extending from the trailing end (72). The needle (70) rotates in a circular path defined by the needle track (84) and between the arms (93A, B). Recessed features (74) may be provided to facilitate the needle driver (86) to engage and drive the needle (70). The needle (70) is captured in the needle track (84) by the needle cover (83). The cage (87) slides over the cartridge body to attach the needle cover (83) against the lower body (81).

Figure 3:
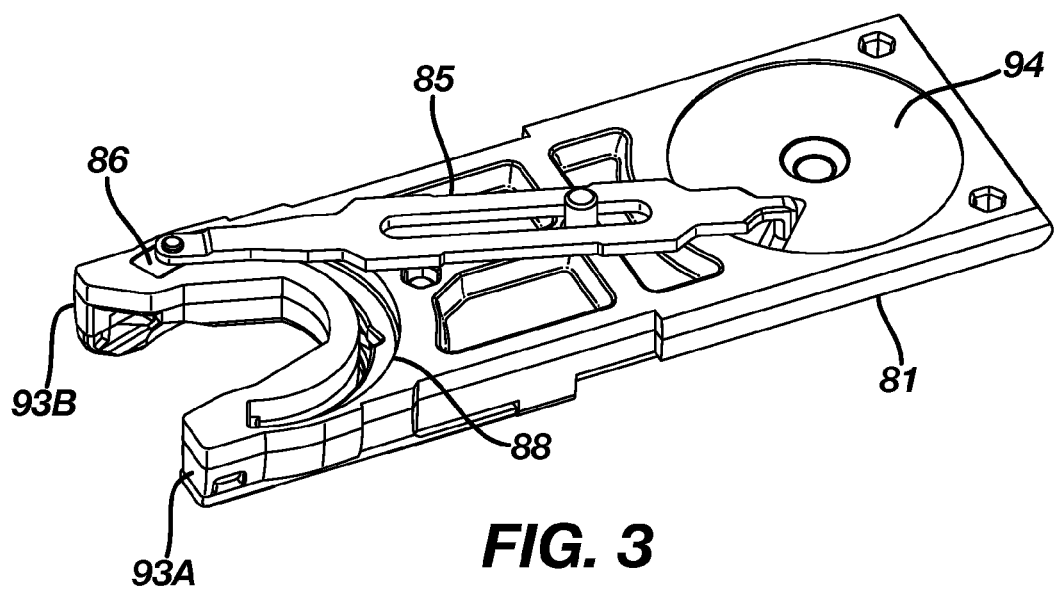
FIG. 3 depicts a perspective view of a transmission for driving a needle.

FIG. 3 illustrates an embodiment of a drive stroke of the transmission in the cartridge (90) for driving a needle (70) in a circular path. The needle driver (86) rides in the carrier track (88) and extends into the needle track (84) to engage and drive the needle (70). The link (85) connects the rotary input (94) to the needle driver (86). Counterclockwise rotation of the rotary input (94) will translate the needle driver (86) clockwise along the carrier track (88) driving the needle (70) clockwise until it reaches the other end of its stroke in the carrier track (88). In this embodiment, the drive stroke rotates the needle (70) in its circular path about 180 degrees. For the return stroke, the sequence can be reversed by rotating the rotary input (94) clockwise, which will translate the needle driver (86) counterclockwise in the carrier track (88) while the needle (70) remains stationary. Thus, a sequence of drive and return strokes will rotate the needle (70) in a circular path.

Figure 4:
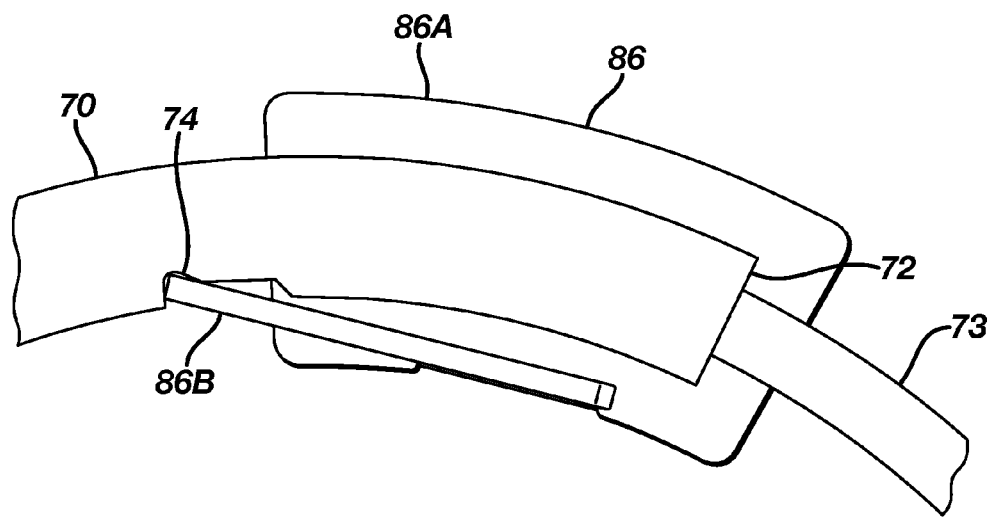
FIG. 4 depicts a needle driver engaging a needle.

FIG. 4 illustrates a detailed view of the needle driver (86) engaging the needle (70). The needle driver (86) comprises a carrier (86A) and a driver (86B). The carrier (86A) is dimensioned to slideably fit in the carrier track (88). The driver (86B) is attached to the carrier (75) and is operative to engage the needle (70) at an oblique angle. Leftward movement of the needle driver (86) will cause the driver (86B) to engage the feature (74) during the drive stroke. When so engaged, the needle (70) will slide in the needle track (84) in unison with the needle driver (86). Due to the oblique angle, rightward movement of the needle driver (86) will disengage the driver (86B) from the feature (74) and slide over the stationary needle (70) during the return stroke.

Further details, explanations, examples, and alternative embodiments of surgical suturing devices and subcomponents of the foregoing are disclosed in co-owned U.S. application Ser. No. 13/832,595 filed 15 Mar. 2013 and application Ser. No. 14/297,993 filed 6 Jun. 2014. The foregoing applications are incorporated herein by reference.

Figure 5:
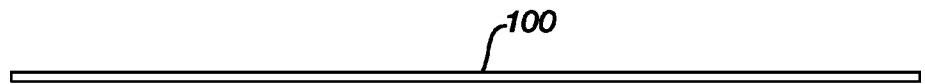
FIG. 5 depicts a needle body during a fabrication process.

FIGS. 5-14 illustrate a method to fabricate the needle (70). Wire is fed off a spool, straightened, and cut to an initial length as shown in FIG. 5 to define an elongate body (100) having a longitudinal axis and a cross-sectional circumference. Many suitable wire materials may be used and may have a variety of different sizes and cross-sectional shapes. A typical wire may have a cross-sectional area between about $3 \times 10^{-5}$ to about 0.005 $in^2$. In the embodiment depicted in FIG. 5, the wire is a stainless steel alloy having a circular cross-section with a nominal diameter of about 0.029 inches and a body (100) length of about 3 inches.

Figure 6:
FIG. 6 depicts a needle body during a fabrication process.

In FIG. 6, a tail (102) is formed on the trailing end of the body (100) for clocking and holding the body (100) during the fabrication process. In this embodiment, the tail (102) is bent generally normal to the body (100), but oblique or other tail shapes are also contemplated.

Figure 7:
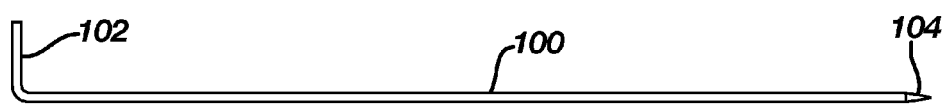
FIG. 7 depicts a needle body during a fabrication process.

In FIG. 7, the point (104) is ground on the leading end of the body (100) to the desired shape for the leading end (71) of the needle (70).

Figure 8:
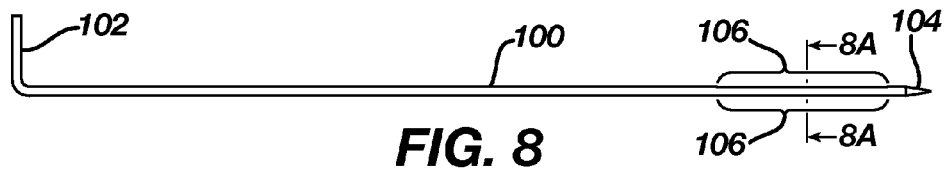
FIG. 8 depicts a needle body during a fabrication process.
Figure 8A:
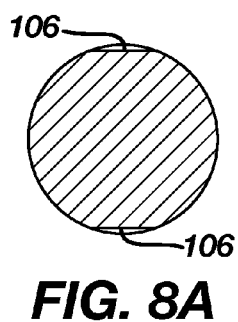
FIG. 8A depicts a cross-sectional view of a needle body from FIG. 8.

In FIGS. 8 and 8A, one or more flats (106) are pressed on body (100). The flats (106) may serve as reference or indexing surface as the body is processed during subsequent steps. The flats (106) may also serve as a reference or indexing surface to hold the needle (70) square within the needle track (84). In this embodiment, two longitudinal flats (106) are arranged at antipodal locations, with the top one flat (106) being circumferentially aligned with the tail (102). In this embodiment, the flats (106) are about equal in length and longitudinally coextensive. Other configurations of the flats (106) are also contemplated.

Figure 9:
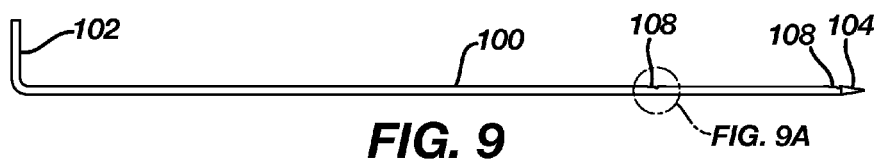
FIG. 9 depicts a needle body during a fabrication process.
Figure 9A:
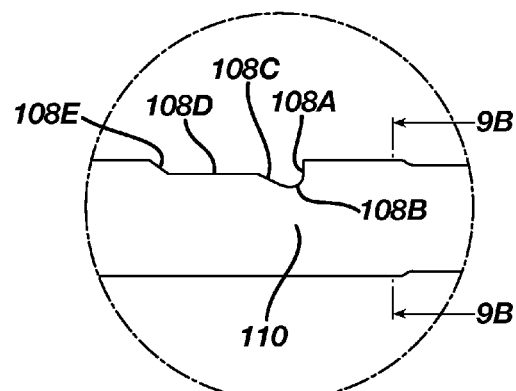
FIG. 9A depicts a detailed view of a drive feature from FIG. 9.
Figure 9B:
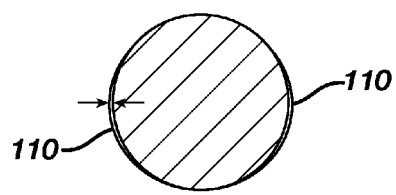
FIG. 9B depicts a cross-sectional view of a needle body from FIG. 9A.

In FIGS. 9 and 9A-B, a plurality of recessed features (108) are formed into the body (100). In this embodiment two features (108) are formed at locations longitudinally spaced from the flats (106) such that the flats are interposed between the features (108). In this embodiment, the features (108) are circumferentially aligned with the top flat (106) and the tail (102). In this embodiment, the leading side of each feature (108) has a step portion (108A) that descends into a valley portion (108B). The step portion (108A) is transverse the longitudinal axis. The depth of the valley portion (108B) is preferably about 5 to 35% the diameter of the body (100) (about 0.003 to 0.009 inches in this example), and more preferably about 15 to 25%. A tiered surface defined by portions (108C-E) rises from the trailing side of the valley portion (108B). Oblique portions (108C, 108E) are arranged at an oblique angle relative the longitudinal axis of the body (100). Flat portion (108D) is intermediate the oblique portions (108C, 108E) and is generally parallel with the longitudinal axis of the body (100). The configuration of the flat portion (108D) and oblique portions (108C, 108E) facilitate a smooth transition of the driver (86B) from the valley portion (108B). Preferably, portions (108A-E) transition to one another with radiuses greater than about 0.002 inches to reduce stress concentrations and to reduce wear on tooling.

In this embodiment the features (108) are formed by plastically deforming the body (100). For instance, a die may be used in a pressing or rolling operation on the body (100) to form the features (108). A plastically deforming operation offers several advantages over techniques involving the removal of material, such as cutting or grinding operations. First, the cross-sectional area will remain substantially the same along the length of the body (100) around the feature (108) resulting in improved strength. Second, plastically formed features (108) are more reliable and reproducible, and capable of faster production. Third, material will be displaced away from the feature (108) resulting in a pair of protuberances (110) projecting outwardly from the body (100). The protuberances (110) are adjacent to and circumferentially offset on either side of the feature (108), and longitudinally coincide with the feature (108). Preferably, the apex of the protuberances (110) longitudinally coincide with the valley portion (108B). The protuberances (110) help center the needle (70) in the track (84), thus facilitating proper alignment of the needle (70) during the drive and return strokes. The height on the protuberances (110) will vary depending upon the gauge of the body (100) and the depth of the feature (108), but each protuberance (110) preferably projects outward about 3-10% the diameter of the body (100) (about 0.001-0.003 inches in this example), and more preferably about 6-8%, as generally shown by the arrows in FIG. 9B. Finally, the spacing of the features (108) may be made very precisely and reproducibly using a single piece die, so the location of features (108) will remain identically spaced from needle-to-needle over the life span of the tooling.

Figure 10:
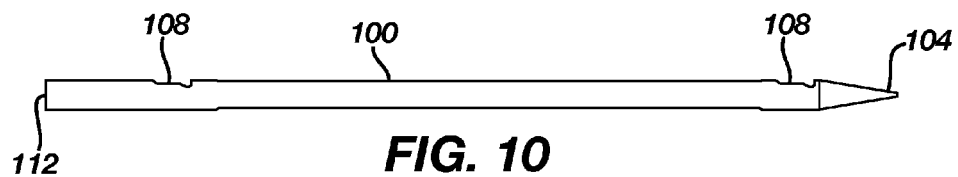
FIG. 10 depicts a needle body during a fabrication process.

In FIG. 10, the body (100) is cut at the trailing end (112) to the final length of the needle (70).

Figure 11:
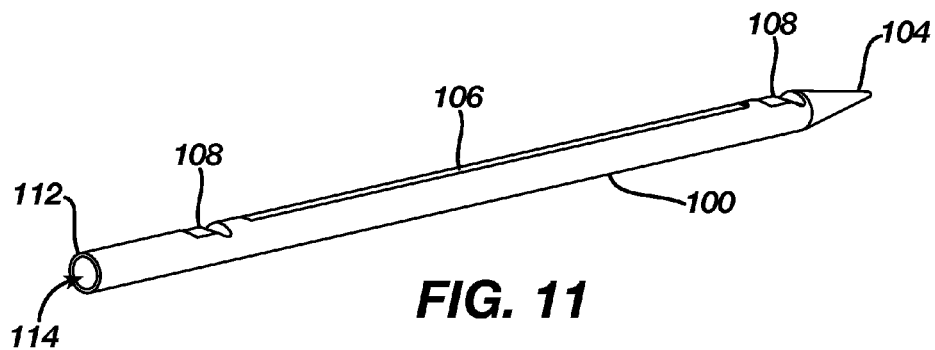
FIG. 11 depicts a needle body during a fabrication process.

In FIG. 11, a hole is drilled in the trailing end (112) to create a barrel (114).

Figure 12:
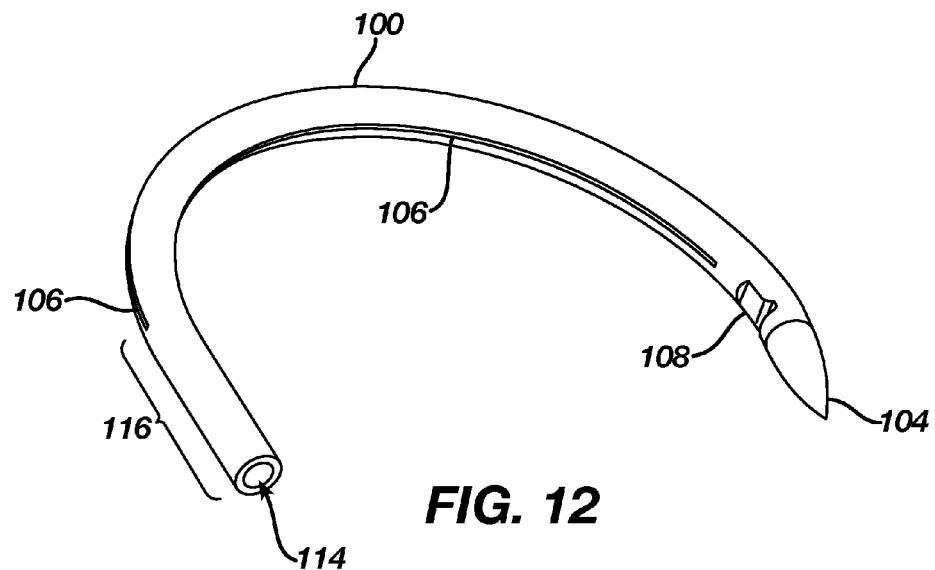
FIG. 12 depicts a needle body during a fabrication process.

In FIG. 12, the body (100) is bent to the desired arcuate shape. In this embodiment, the body (100) is curved along a circular path; however, the trailing portion (116) with the barrel (114) is kept straight. The diameter of the circular arc may vary based on the desired size of the needle (70), but in this embodiment the centerline radius of curvature is about 0.2 inches. The curved body (100) defines a plane dividing upper and lower faces on the body (100). The flats (106) are positioned on the medial and lateral faces of the body (100), with the features (108) oriented on the medial face and the protuberances projecting outwardly from the upper and lower faces of the body (100). The flats (106) may be referenced prior to bending to facilitate the desired orientation of the features (108). It should be appreciated, however, that the orientation of the features (108) may be changed (e.g., on the upper, lower, or lateral faces) depending upon where the needle driver (86) is intended to engage the needle (70). The body (100) may be cleaned, heat treated, electropolished, and/or coated with a lubricious silicone. The silicone chemistry may be characterized as a polydimethylsiloxane with functionalized end groups to provide a combination of lubricity and multiple pass performance.

Figure 13:
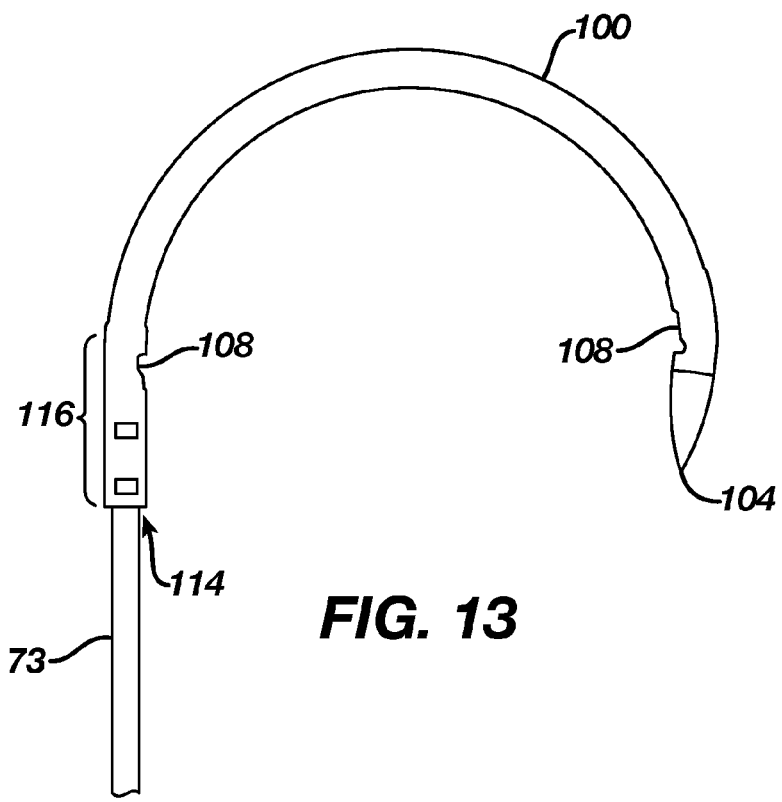
FIG. 13 depicts a needle body during a fabrication process.

In FIG. 13, suture (73) is inserted into the barrel (114) and fixed to the body (100) with a swaging operation; however, other fixation techniques may also be used such as welding, adhesives, etc.

Figure 14:
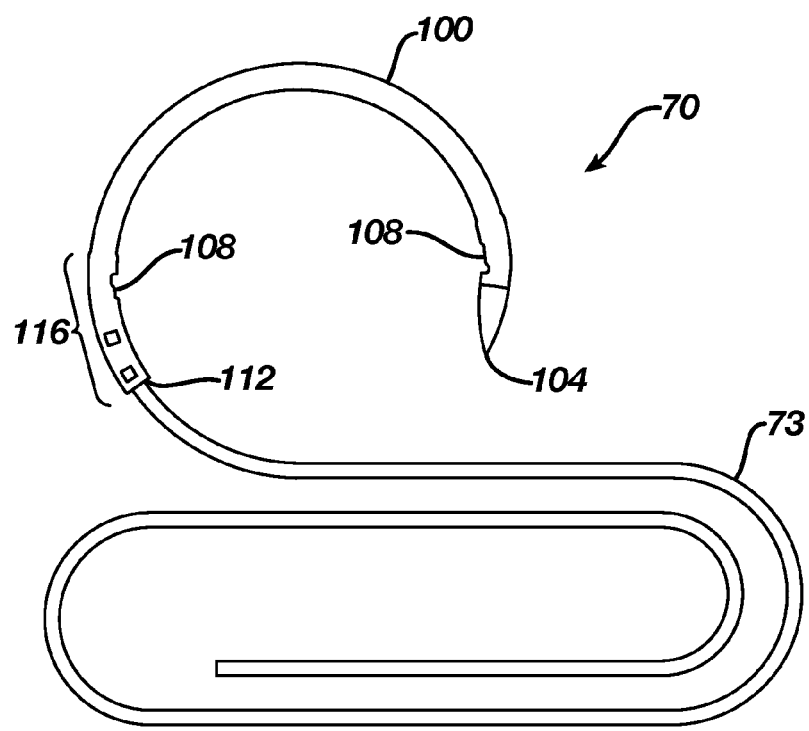
FIG. 14 depicts a needle body during a fabrication process.

In FIG. 14, the trailing portion (116) is bent along the same circular arc as the remainder of the body (100), thus completing a fabricated needle (70). The features (108) are positioned at antipodal points on the circular arc, and the angular span between the point (104) and trailing end (112) is about 225 to 250 degrees.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Similarly, some steps may be eliminated or performed in an alternative sequence. Accordingly, the scope of the present invention should be considered in terms of the following claims and is understood not to be limited to the details of structure, materials, or acts shown and described in the specification and drawings.

The invention claimed is:

1. A surgical needle adapted for use with a circular needle applier having a needle driver, the surgical needle comprising:

an elongate body curved along a circular arc in a plane, the elongate body having a leading end, a trailing end, a longitudinal axis between the leading and trailing ends, a cross-sectional circumference, an upper face, a lower face, a medial face, and a lateral face;

a first recessed feature on the medial face of the body adapted to be engaged by a needle driver;

a first pair of protuberances projecting outwardly from the upper and lower faces of the body, the first pair of protuberances being longitudinally coincident with the first recessed feature;

a second recessed feature on the medial face of the body adapted to be engaged by a needle driver, the second recessed feature being located at the antipodal point of the circular arc relative the first recessed feature; and a second pair of protuberances projecting outwardly from the upper and lower faces of the body, the second pair of protuberances being longitudinally coincident with the second recessed feature.

\* \* \* \* \*